United States Patent
Daugs

(10) Patent No.: US 6,777,562 B1
(45) Date of Patent: Aug. 17, 2004

(54) PREPARATION OF A TRANS-CALANOLIDE KETONE INTERMEDIATE AND CHIRAL SEPARATION OF CALANOLIDE ALCOHOLS TO GIVE RACEMIC CALANOLIDE A

(75) Inventor: Edward D. Daugs, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/369,984

(22) Filed: Feb. 19, 2003

(51) Int. Cl.$^7$ ............................................. C07D 493/14
(52) U.S. Cl. ....................................................... 549/277
(58) Field of Search ........................................ 549/277

(56) References Cited

U.S. PATENT DOCUMENTS

| | | | |
|---|---|---|---|
| 5,489,697 A | 2/1996 | Boulanger et al. ........... | 549/278 |
| 6,277,879 B1 | 8/2001 | Xu et al. ..................... | 514/453 |

OTHER PUBLICATIONS

Cardellina, J. H. et al., "Resolution and Comparative Anti–HIV Evaluation of the Enantiomers of Calanolides A and B$^1$," *Bioorganic and Medicinal Chemistry Letters*, vol. 5, No. 9, 1995, pp. 1011–1014.

Ishikawa, T. et al., "Cesium Fluoride–Induced Intramolecular Michael Addition: Highly Diastereoselective Ring Construction of a trans–2,3–Dimethylchroman–4–one," *Journal of Organic Chemistry*, vol. 61, 1996, pp. 6484–6485.

Flavin, M. T. et al., "Synthesis, Chromatographic Resolution, and Anti–Human Immunodeficiency Virus Activity of (±)–Calanolide A and its Enantiomers," *Journal of Medicinal Chemistry*, vol. 39, 1996, pp. 1303–1313.

Gemal, A. G. and Luche, J. L., "Lanthanoids in Organic Synthesis. 6. The Reduction of a–Enones by Sodium Borohydride in the Presence of Lanthanoid Chlorides: Synthetic and Mechanistic Aspects, " *J. Am. Chem. Soc.*, vol. 103, 1981, 5454–5459.

*Primary Examiner*—Bernard Dentz

(57) ABSTRACT

The method of the invention comprises a process for synthesizing a trans-calanolide A ketone intermediate used in the synthesis of racemic trans-calanolide A. The invention further comprises a method for removing a racemic calanolide B diastereomer from a mixture of calanolide A and calanolide B diastereomers formed in the last step of the synthesis of calanolide A by crystallization.

7 Claims, No Drawings

PREPARATION OF A TRANS-CALANOLIDE KETONE INTERMEDIATE AND CHIRAL SEPARATION OF CALANOLIDE ALCOHOLS 5,489,697, Feb. 6, 1996. M. T. Flavin, et.al; *J. Med. Chem.* 39, 1303 (1996).

FIG. 1. Synthesis of (+)-Calanolide

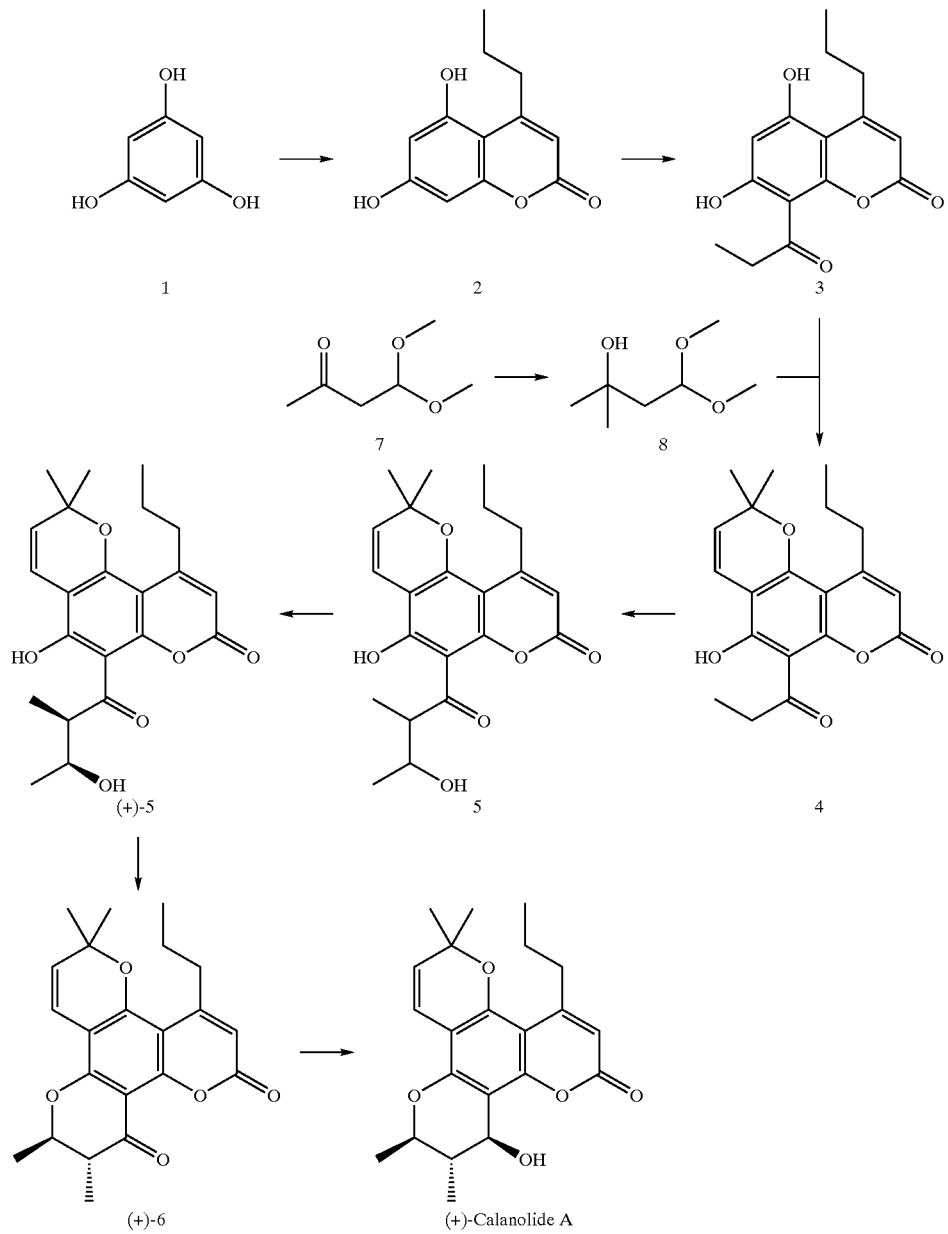

TO GIVE RACEMIC CALANOLIDE A

The invention relates to a process for synthesizing a trans-calanolide ketone intermediate, and for separating the two diastereomers of the product alcohol from one another to give racemic calanolide A.

(+)-Calanolide A is an HIV-1 specific reverse transcriptase inhibitor under investigation for the treatment of AIDS, Z. Q. Xu, M. T. Flavin, and D. Zembower; U.S. Pat. No. 6,277,879, Aug. 21, 2001. The current state of the art for synthesis of (+)-calanolide A is outlined in FIG. 1 below, Z. Q. Xu, M. T. Flavin, and D. Zembower, U.S. Pat. No. 6,277,879, Aug. 21, 2001, and W. A. Boulanger, M. T. Flavin, A. Kucherenko, A. K. Sheynkman; U.S. Pat. No.

In this route, intermediate 5 is resolved by a time-consuming enzyme-catalyzed kinetic resolution using an equivalent weight of lipase AK with vinyl acetate. A chromatographic separation is required to separate the acetate ester of (−)-5 from desired (+)-5. According to the current state of the at, the trans-calanolide ketone intermediate (+)-6 is produced by the treatment of (+)-5 with diethyl azodicarboxylate (DEAD) and triphenylphosphine under Mitsunobu reaction conditions. A second, more difficult chromatographic purification is required to remove the by-products diethyl hydrazinodicarboxylate and triphenylphosphine oxide from the desired trans-calanolide ketone. Reduction of the ketone function to the alcohol using sodium borohydride with cerium chloride (Luche conditions, A. L. Gemal and J. L. Luche; *J. Am. Chem. Soc.* 103, 5454 (1981)) gives crude (+)-calanolide A still containing by-products from the Mitsunobu reaction. The product of the Luche reduction also contains the diastereomer (+)-calanolide B. The crude (+)-calanolide A is purified by preparative chromatography to remove Mitsunobu by-products and (+)-calanolide B, to give an isolated yield of 17% from chromene intermediate 4.

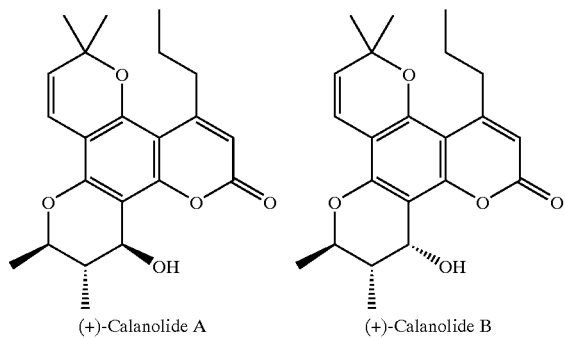

(+)-Calanolide A          (+)-Calanolide B

Separation of (+)-calanolide A from the racemate by semipreparative chiral HPLC had been used previously to afford small quantities of the pure stereoisomer, W. A. Boulanger, M. T. Flavin, A. Kucherenko, A. K. Sheynkman; U.S. Pat. No. 5,489,697, Feb. 6, 1996. M. T. Flavin, et.al; *J. Med. Chem.* 39, 1303 (1996), and J. H. Cardellina II, H. R. Bokesh, T. C. McKee, M. R. Boyd; *Bioorg. Med. Chem. Lett.* 5, 1011 (1995). A larger scale separation has been proposed as an alternative method of preparation to avoid the lengthy enzymatic resolution step. To this end, a practical method of preparation of racemic calanolide A is desired.

The process of the invention comprises a new scaleable process for synthesizing the trans-calanolide A ketone intermediate. The process comprises the steps of 1) reacting a chromene intermediate in methylene chloride solution, stepwise, with titanium tetrachloride followed by diisopropylethylamine followed by acetaldehyde, 2) quenching the product into cold aqueous ammonium chloride, 3) washing the organic phase with an acidified water wash, 4) drying the organic phase with magnesium sulfate, 5) filtering, 6) evaporating the solvent, 7) treating the aldol intermediate obtained with dimethylformamide dimethylacetal in tetrahydrofuran, 8) treating with saturated brine and water, 9) removing the aqueous phase and solvent, 10) equilibrating with triethylamine containing t-amyl alcohol, and 11) removing the crystalline ketone via filtration. The method of the invention eliminates the tedious enzymatic resolution and the difficult chromatographic purification steps required in the current process.

According to the synthesis process of the invention, the racemic trans-calanolide ketone may be produced by treatment of an aldol intermediate with dimethylformamide dimethyl acetal (DMFDMA) followed by equilibration using triethylamine in t-amyl alcohol. The desired trans-calanolide ketone crystallizes out of the solution and can be isolated by filtration. The intermediate does not require isolation for this procedure, and the byproducts produced by prior art processes are not present. Therefore, the process of the invention does not require any chromatographic purification to remove byproducts and gives similar isolated yields.

The invention further comprises a method for removing the racemic calanolide B diastereomer from a mixture of calanolide A and calanolide B diastereomers formed in the last step of the synthesis of calanolide A. The method comprises the steps of 1) repeatedly recrystallizing the calanolide B in the mixture from toluene, and 2) concentrating the combined mother liquors and recrystallizing the residue from aqueous 2-propanol to isolate purified racemic calanolide A.

The process of the invention comprises a new scaleable process for synthesizing the trans-calanolide A ketone intermediate used in the synthesis of racemic trans-calanolide A. The process comprises the steps of 1) reacting a chromene intermediate in methylene chloride solution, stepwise, with titanium tetrachloride followed by diisopropylethylamine followed by acetaldehyde, 2) quenching the product into cold aqueous ammonium chloride, 3) washing the organic phase with an acidified water wash, 4) drying the organic phase with magnesium sulfate, 5) filtering, 6) evaporating the solvent, 7) treating the aldol intermediate obtained with dimethylformamide dimethylacetal in tetrahydrofuran, 8) treating with saturated brine and water, 9) removing the aqueous phase and solvent, 10) equilibrating with triethylamine containing t-amyl alcohol, and 11) removing the crystalline ketone via filtration. The process of the invention eliminates the tedious enzymatic resolution and the difficult chromatographic purification steps required in the current process.

Prior art taught that base-catalyzed condensation of an aldol-type intermediate may be used for the preparation of a similar ring structure, T. Ishikawa, Y. Oku, K. I. Kotake, H. Ishii; *J. Org. Chem.* 61, 6484 (1996). However, use of cesium fluoride or triethylamine with the aldol condensation product 5 gave only partial conversion, along with decomposition products. Use of a dehydrating agent led to formation of the alkene 9, which was followed by cyclization to give the desired ring structure (FIG. 2).

FIG. 2. Dehydration and Cyclization of Aldol Intermediate.

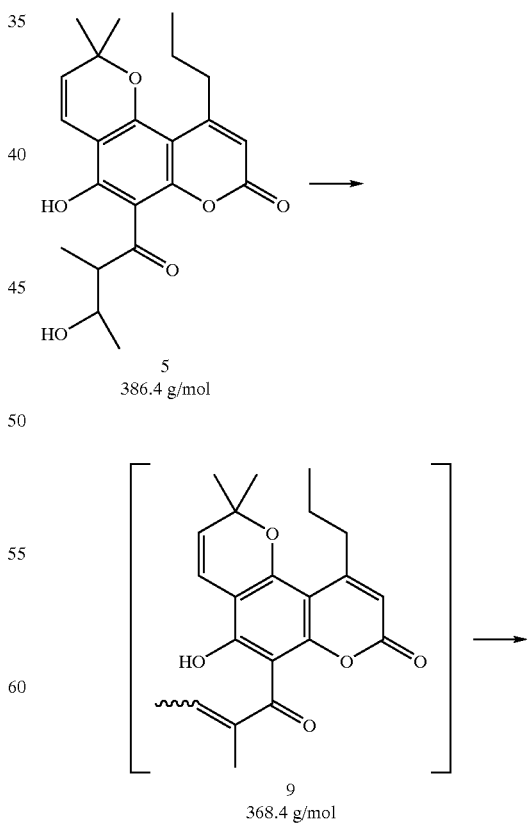

5
386.4 g/mol 9
368.4 g/mol

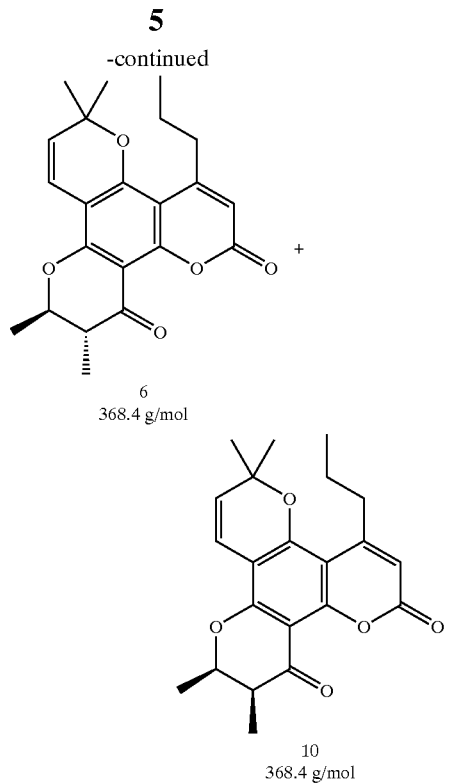

6
368.4 g/mol 10
368.4 g/mol

According to the synthesis process of the invention, the racemic trans-calanolide ketone 6 may be produced by treatment of the aldol intermediate 5 with dimethylformamide dimethyl acetal (DMFDMA) followed by equilibration using triethylamine in t-amyl alcohol. The desired trans-calanolide ketone crystallizes out of the solution and can be isolated by filtration. The desired trans-calanolide ketone has a low solubility in solvents such as triethylamine and t-amyl alcohol, and so crystallizes from solution. Additionally, equilibration of the cis-calanolide ketone isomer 10 also formed in the cyclization reaction to the trans-calanolide ketone occurs readily in basic solution. The overall equilibrium is driven to produce the desired trans-calanolide form by removal of this form from solution by crystallization. The by-products produced by the prior art processes are not present in this process. Therefore, the process of the invention does not require any chromatographic purification to remove by-products, and gives similar isolated yields.

The aldol condensation of 4 with acetaldehyde in the presence of titanium tetrachloride and diisopropylethylamine in methylene chloride gives 5 as shown in FIG. 3 below. The reaction is mediated by initial complexation of the product with titanium tetrachloride. A decrease in either the titanium tetrachloride or the diisopropylethylamine unit ratio led to lower conversions. Reaction mixtures with lower conversions could not be driven to completion with additional quantities of titanium tetrachloride, diisopropylethylamine, or acetaldehyde. Although the conversion was reported to be approximately 90%, the isolated yield was only 47%, presumably due to the previously observed retro-aldol reaction to reform starting material during the work-up and chromatographic purification.

FIG. 3. Adol Condensation of 4 to Give 5.

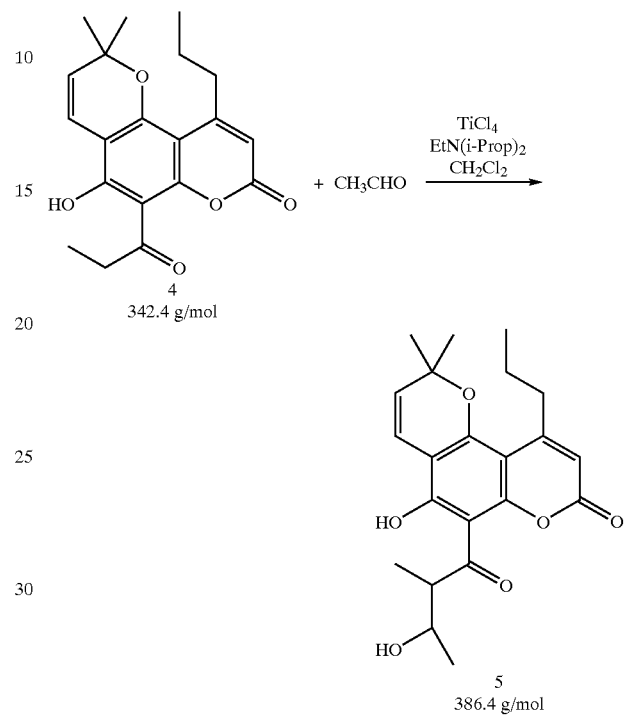

4
342.4 g/mol 5
386.4 g/mol

The reaction was carried out by addition of titanium tetrachloride, followed by diisopropylethylamine, followed by acetaldehyde to a methylene chloride solution of 4 at reaction temperatures of 0–10° C. The reaction mixture was quenched into cold (0–10° C.) aqueous ammonium chloride. A water wash of the methylene chloride solution was used to remove the residual titanium tetrachloride/diisopropylethyl-amine complex, but it was found to increase the level of starting material as well. Acidification of the wash solution, however, gave a mixture that was stable to standing overnight. The methylene chloride phase was dried with magnesium sulfate before a removal of the solvent by evaporation at ambient temperature.

Reaction conversion appeared to be sensitive to the unit ratios of titanium tetrachloride, diisopropylethylamine, and methylene chloride, and the amount of titanium tetrachloride required appeared to vary between batches of 4. Six different batches of 4 (SMA through SMF) were evaluated. Reaction loadings, along with the maximum temperatures reached during each reagent addition, are listed in Table 1.

TABLE 1

Aldol Reaction Conditions and Product Conversions.

| Evaluation | S.M. | Loading g/g of 4 | | | | T max ° C. | | | HPLC Area % | |
|---|---|---|---|---|---|---|---|---|---|---|
| | | $CH_2Cl_2$ | $TiCl_4$ | Amine | $CH_3CHO$ | $TiCl_4$ | Amine | $CH_3CHO$ | 4 | 5 |
| A | SMA | 13.8 | 2.10 | 0.84 | 0.95 | 5 | 10 | — | 18 | 71 |
| B | SMA | 34.8 | 1.65 | 0.81 | 0.79 | 5 | 8 | 5 | 4.4 | 91.6 |
| C | SMA | 34.8 | 1.65 | 0.61 | 0.79 | 5 | 7 | 7 | 2.5 | 95.3 |

TABLE 1-continued

Aldol Reaction Conditions and Product Conversions.

| | | Loading g/g of 4 | | | | T max ° C. | | | HPLC Area % | |
|---|---|---|---|---|---|---|---|---|---|---|
| Evaluation | S.M. | CH$_2$Cl$_2$ | TiCl$_4$ | Amine | CH$_3$CHO | TiCl$_4$ | Amine | CH$_3$CHO | 4 | 5 |
| D | SMA | 34.8 | 1.72 | 0.61 | 0.79 | 5 | 7 | 7 | 0.5 | 96.2 |
| E | SMA | 27.3 | 2.06 | 0.82 | 0.84 | 6 | 8 | — | 3.8 | 91.7 |
| F | SMA | 19.0 | 2.03 | 0.81 | 0.86 | 12 | 20 | 17 | 41 | 54 |
| G | SMA | 19.0 | 2.03 | 0.81 | 0.86 | −13 | −13 | −8 | 26 | 59 |
| H | SMB | 19.0 | 2.03 | 0.Bi | 0.86 | −18 | −13 | −10 | 3.2 | 89.9 |
| I | SMB | 25.7 | 2.06 | 0.83 | 0.84 | 5 | 16 | — | 16 | 73 |
| J | SMC | 25.0 | 1.67 | 0.84 | 0.79 | −7 | 6 | 3 | 0.7 | 96.6 |
| K | SMD | 25.0 | 2.00 | 1.00 | 0.79 | −15 | −5 | −5 | 1.4 | 95.8 |
| L | SME | 25.0 | 2.00 | 1.00 | 0.79 | 0 | 4 | 14 | 2.8 | 93.8 |
| M | SME | 25.0 | 2.00 | 1.32 | 0.79 | 0 | 5 | 8 | 4.2 | 71 |
| N | SMF | 25.0 | 1.67 | 0.84 | 0.79 | −7 | −6 | −3 | 17 | 77 |
| O | SMF | 25.0 | 1.67 | 0.84 | 0.79 | 0 | 6 | 6 | 14 | 83 |
| P | SMF | 25.0 | 2.00 | 1.00 | 0.79 | 2 | 13 | 6 | 2.3 | 92.7 |

From this data, higher reaction concentrations appear to be detrimental to conversion (Evaluation A). A methylene chloride unit ratio of 25 consistently gave good results. While a titanium tetrachloride unit ratio of 1.67 gave less than 5 area % of 4 from SMA and SMC, approximately 15% starting material remained from SMF (Evaluation N and Evaluation O). A higher titanium tetrachloride unit ratio of 2 gave complete reaction with this material (Evaluation P). An increase in the diisopropylethylamine unit ratio gave a higher level of other impurities (Evaluation M). Higher reaction temperatures appeared to also contribute to a lower conversion (Evaluation F).

When 5 is treated with a dehydration agent such as dimethylformamide dimethyl acetal (DMDMA) in THF, it forms the alkene 9 (FIG. 2). After stirring overnight at ambient temperature, 9 cyclized to a mixture of racemic 6 and 10. It was found that the desired trans-ketone 6 had a low solubility in triethylamine or t-amyl alcohol, and that equilibration of 10 to 6 occurred readily in basic solution (a 6/10 ratio of approximately 3/1 at equilibration).

The THF reaction mixture was washed with brine to minimize decomposition by quenching any remaining DMDMA. THF was then exchanged for triethylamine. A small amount of t-amyl alcohol was added to aid in the solubility of reaction mixture oil in triethylamine. By stirring the reaction mixture containing 6 and 10 in triethylamine at 40 to 45° C., the equilibration of 10 to 6 was driven as 6 crystallized out of solution.

Progress of the reactions can be seen through the data of Table 2. Starting from material that was 95 to 98 area % of 4; approximately 90 area % of the aldol product 5 was generally found following the ammonium chloride quench. The best results were obtained when minimal 5 was detected a few hours after the DMDMA addition (Evaluation Q). Stirring this reaction mixture overnight at 20° C. gave an approximately 50/50 mixture of 6 and 10. At 0° C., conversion of the enone 9 was incomplete (Evaluation J). Heating the mixture of ketones 6 and 10 overnight in triethylamine gave a slurry containing from 60 to 80 area % of 6.

TABLE 2

HPLC Analysis of Reaction Intermediates to Give 6.

| | | | HPLC Area % | | | | |
|---|---|---|---|---|---|---|---|
| Evaluation | Sample | | 4 | 5 | 9 | 10 | 6 |
| Q | Starting Material | SMC | 98.1 | | | | |
| J | | SMC | 98.1 | | | | |
| N | | SMF | 94.8 | | | | |
| P | | SMF | 94.8 | | | | |
| L | | SME | 96.4 | | | | |
| K | | SMD | 98.6 | | | | |
| Q | Aldol, Quenched | | 1.5 | 95.8 | | | |
| J | | | 1.0 | 93.5 | | | |
| N | | | 20.4 | 74.0 | | | |
| P | | | 1.4 | 88.2 | | | |
| L | | | 3.1 | 93.3 | | | |
| K | | | 1.2 | 95.8 | | | |
| Q | DMDMA | 1 hr, 10° C. | 6.0 | 2.6 | 54.9 | 2.9 | 19.2 |
| J | | Overnight, 0° C. | | | 70.5 | 0.6 | 17.8 |
| N | | 2 h, 0 to 20° C. | 27.1 | 16.4 | 30.4 | | 12.9 |
| | | Overnight, 20° C. | | 7.9 | 6.7 | 32.4 | 31.1 |
| P | | 2 h, 0 to 20° C. | 6.7 | 8.8 | 33.2 | 9.0 | 18.5 |
| L | | Overnight, 20° C. | | 4.95 | 34.2 | 41.5 | |
| K | | Overnight, 20° C. | | | 3.0 | 39.6 | 47.6 |
| J | Et3N | ca. 1 hr | | | 11.3 | 31.8 | 31.4 |
| N | | | | | | 21.6 | 39.6 |
| P | | | | | | 13.5 | 51.1 |
| L | | | | | | 33.6 | 50.7 |

TABLE 2-continued

HPLC Analysis of Reaction Intermediates to Give 6.

| Evaluation | Sample | | | HPLC Area % | | | | |
|---|---|---|---|---|---|---|---|---|
| | | | | 4 | 5 | 9 | 10 | 6 |
| K | | | | | | | 25.2 | 59.3 |
| J | Et3N | Overnight, 40° C. | | | | | 6.6 | 65.1 |
| P | | | | | | | 7.6 | 63.7 |
| L | | | | | | | 9.6 | 79.4 |
| K | | | | | | | 11.5 | 77.0 |

The reaction mixture is cooled to ambient temperature before isolation of 6 by vacuum filtration; the filtercake is washed with a small amount of t-amyl alcohol, which removes much of the color. The product is generally purified by digestion or recrystallization in ethanol at reflux. Isolated yields ranged from 24 to 47%, and are summarized in Table 3. The lowest yield (Evaluation N) was obtained from the batch that had incomplete conversion from the aldol reaction. Although the aldol reaction product contained approximately 20% residual 4, the subsequent reactions did not fail as the material was carried forward, and 6 was successfully crystallized from the triethylamine reaction mixture.

TABLE 3

Isolated Yields and HPLC Analyses of 6.

| Evaluation | S.M. | HPLC Area % | | % Yield |
|---|---|---|---|---|
| | | 6 | 14 | |
| Q | SMC | 98.2 | 1.4 | 46 |
| J | SMC | 97.4 | 2.0 | 46 |
| K | SMD | 97.2 | 2.2 | 45 |
| L | SME | 95.7 | 2.2 | 34 |
| R | SME | 97.6 | 1.1 | 47 |
| N | SMF | 97.7 | 0.41 | 24 |

Reduction of 6 with sodium borohydride in ethanol gives a mixture of calanolide A and calanolide B (FIG. 4). Use of cerium chloride (Luche conditions) at −10 to −40° C. gave 90% calanolide A over calanolide B. Chiral HPLC with a Daicel Chiralpak AD column and 2.5% methanol in pentane was used to determine the calanolide isomer ratios. With this system, one of the calanolide B isomers generally co-eluted with the first calanolide A isomer, although separation of the peaks was observed on occasion. The calanolide B level was determined by doubling the area % of the second, always separated, calanolide B peak.

FIG. 4. Reduction to Calanolide A.

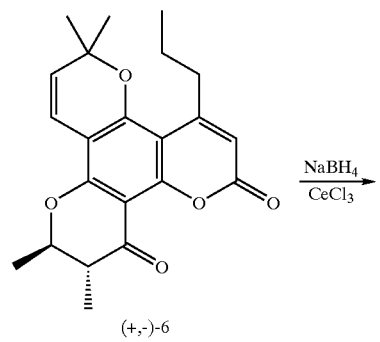

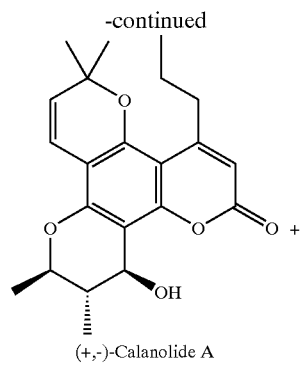

(+,-)-Calanolide A

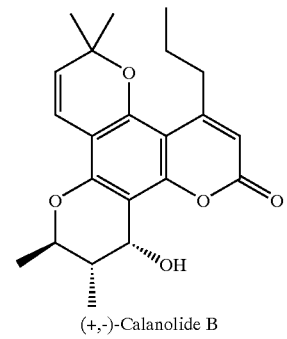

(+,-)-Calanolide B

The invention further comprises a method for removing a racemic calanolide B diastereomer from a mixture of calanolide A and calanolide B diastereomers formed in the last step of the synthesis of calanolide A. The method comprises the steps of 1) repeatedly recrystallizing the calanolide B in the mixture from toluene, and 2) concentrating the combined mother liquors, and recrystallizing the residue from aqueous 2-propanol to isolate purified racemic calanolide A.

Prior art used a chromatographic purification for separation of calanolide B from the calanolide A, Z. Q. Xu, M. T. Flavin, and D. Zembower; U.S. Pat. No. 6,277,879, Aug. 21, 2001. An additional chromatographic separation using a chiral stationary phase is then necessary to separate the (−)-calanolide A from the desired (+)-calanolide A. Thus, two chromatographic separations are required to isolate the desired (+)-calanolide A from the product of the Luche reduction. Large scale chromatographic separations are typically more tedious and less economical than separations by crystallization.

Repetitive recrystallization of the isolated solid according to the method of the invention gave up to a 50/50 mixture of calanolide A and calanolide B, depleting the mother liquor in calanolide B. Aqueous 2-propanol, which was found to deplete the level of calanolide B in the isolated solid but not at a level to be useful as a sole separation method, was used to isolate the purified racemic calanolide A from the mother liquors. A 66% recovery of 98.2% pure racemic calanolide A was obtained from feed containing 10.6% of calanolide B using this method.

Ketone 6 has a low solubility in the ethanol reaction solvent, so the reaction mixture remained a slurry throughout the reduction reaction. Addition of toluene gave an initial solution of the ketone, but the reaction was incomplete at a reaction temperature of 20° C.; warming to ambient temperature gave complete reduction in a few hours, with formation of 15 to 20% of calanolide B. Reaction at −60 to −70° C., with or without THF as a co-solvent, gave incomplete reduction until warming to ambient temperature. The calanolide B level was approximately 10% under these conditions.

Reduction reactions in ethanol using powdered sodium borohydride were complete after stirring overnight at −20° C. After a quench of the excess borohydride with acetone, the reaction mixture was poured into aqueous ammonium chloride and the product was extracted into toluene. The solution was dried over magnesium sulfate, filtered, and the solvent was removed to give an oil. Addition of heptane gave a solid. Calanolide B levels for the reaction mixture are shown in Table 4.

Racemic calanolide A could be crystallized from the product oil using a variety of solvents. The results are shown in Table 4. Use of ketone solvents such as acetone and methyl ethyl ketone gave product decomposition, as evidenced by solution darkening and an increased level of impurities observed by HPLC analysis. Decomposition was also observed in methanol, where an increased level of impurities was found in the mother liquor.

TABLE 4

Crystallization of Racemic Calanolide A.

| Evaluation | Solvent | % Calanolide B | | | Yield |
|---|---|---|---|---|---|
| | | Reaction Mix | Isolated | Mother Liquor | |
| S | Methanol | 8.6 | 22.4 | 2.5 | 20% |
| T | Toluene | 12.6 | 26.3 | 2.9 | 35% |
| U | MTBE | 11.3 | 18.7 | | 38% |
| | Second Crop | | 2.2 | 12.9 | 35% |
| V | Heptane | 11.1 | 11.8 | 4.8 | 84% |

Crystallization was found to increase the level of calanolide B in the isolated solid, and so decrease the level in the mother liquor; A second crop of the MTBE crystallization mother liquor afforded a 35% yield of racemic calanolide A containing 2.2% calanolide B. Heptane gave good recovery without a large effect on the calanolide B level.

Crystallization of racemic calanolide A from methanol, toluene, and methyl t-butyl ether were found to enrich the ratio of calanolide B in the isolated solid, thereby decreasing the ratio in the mother liquor. Racemic calanolide A containing at least 10% of calanolide B was found to crystallize from toluene with increasing amounts of calanolide B, up to a maximum of approximately 50%. The ratio of A to B obtained was determined by HPLC analysis at $\lambda=312$ nm. Additionally, the diastereomer ratio was measured by integration of the proton spectra; the peaks for the hydrogen on the alcohol-containing carbon are at 3.92 and 4.25 ppm for calanolide A and calanolide B, respectively. Both HPLC and NMR analyses showed the same ratio of diastereomers, confirming both the molar ratio and an equivalent UV response factor for calanolide A and calanolide B. Results from toluene crystallizations are summarized in Table 5.

TABLE 5

Toluene Crystallization of Racemic Calanolide A.

| | | | HPLC Area % | | | | | |
|---|---|---|---|---|---|---|---|---|
| | | g Tol | Starting Mater. | | Isolated | | Mother Liquor | | |
| Evaluation | T° C. | per g | Cal A | Cal B | Cal A | Cal B | Cal A | Cal B | % Yield |
| T | 23 | 1.3 | 87.40 | 12.60 | 73.70 | 26.30 | 97.10 | 2.90 | 35 |
| W | 25 | 3.7 | 79.80 | 19.70 | 54.80 | 43.60 | 86.50 | 13.20 | 14 |
| X | 25 | 7.2 | 91.20 | 8.80 | 94.26 | 5.74 | 90.24 | 9.72 | 10 |
| Y | 23 | 3.7 | 79.46 | 20.25 | 55.10 | 44.00 | 89.70 | 9.90 | 27 |
| Z | −8 | 3.0 | 79.46 | 20.25 | 60.31 | 39.69 | 97.64 | 1.88 | 47 |
| AA | 1 | 3.0 | 87.67 | 12.32 | 74.75 | 25.25 | 95.44 | 3.93 | 31 |
| BB | 8 | 3.0 | 79.46 | 20.25 | 60.50 | 39.00 | 93.64 | 5.45 | 41 |
| CC | 1 | 4.0 | 60.50 | 39.00 | 48.00 | 51.62 | 89.98 | 9.94 | 62 |

As the calanolide B level in the mother liquor dropped towards 2% by decreasing the isolation temperature or increasing the concentration, loss of calanolide A to the isolated solid increased. Comparing, for example, experiments Evaluations Y and Z, the calanolide level in the isolated solid increased from 55.1 to 60.3% by isolating approximately 20% more as the solid fraction in Evaluation Z, leaving less than 2% of calanolide B in the mother liquor. When the starting material contained 8.8% of calanolide B (Evaluation X), a low recovery of isolated solid that was depleted in calanolide B was obtained.

The concentrations of calanolide A and B in the toluene crystallization mother liquors of Table 6, calculated from the amounts and diastereomer ratios loaded and isolated did not appear to vary markedly with temperature. The concentrations of calanolide in solution decreased from approximately 2% to less than 0.5% with decreasing temperature. Solubilities at 24.5° C. were 13.3 and 3.3 wt %, and at 5° C. were 5.1 and 1.6 wt % for racemic calanolide A and the diastereomeric mixture, respectively. The pure racemate showed approximately four times the solubility of the mixture.

The melting points of the isolated solids obtained from toluene were influenced by the level of calanolide B (Table 6). The highest melting point was found with the material that had the highest level of calanolide B.

TABLE 6

Melting Points of Mixtures of Ricemic Calanolide A and B from Toluene.

| Evaluation | % Cal A | % Cal B | mp ° C. |
|---|---|---|---|
| CC | 48.00 | 51.86 | 151–3 |
| Y | 55.12 | 43.97 | 145–6 |
| AA | 74.75 | 25.25 | 130–4 |
| U | 81.30 | 18.70 | 126–9 |
| DD | 90.97 | 5.54 | 103–5 |
| EE | 98.5 | 1.5 | 128–9 |

Racemic calanolide A was also found to crystallize from aqueous 2-propanol. Unlike the other solvents evaluated, the solid from aqueous 2-propanol was depleted in the level of calanolide B in the isolated solid, increasing the level in the mother liquor.

Microscopic examination of the solid obtained from aqueous 2-propanol showed that the crystals formed long, thin rods. It was best to dry the fluffy white wetcake at ambient temperature, as it would partially liquefy and solidify while vacuum drying at 40° C., forming a hardened mass. A dried sample had a melting range of 113 to 117° C., and contained 4.3 wt % water by Karl Fisher analysis, suggesting that the material may form a hydrate. A 1:1 molar hydrate would contain 4.6 wt % of water.

The solubilities of racemic calanolide A in aqueous 2-propanol at temperatures between about 20 and 50° C. were measured (Table 7). The solubility of calanolide A decreased smoothly to less than 0.5 wt % at 50% aqueous 2-propanol. The low solubilities found at lower temperatures and higher water concentrations make high recoveries from aqueous 2-propanol possible.

TABLE 7

Solubility of Racemic Calanolide A in Aqueous 2-Propanol.

| Temperature | [Water] | [Calanolide A] |
|---|---|---|
| 23° C. | 5 wt % | 4.11 wt % |
| 23 | 10 | 2.84 |
| 23 | 15 | 2.07 |
| 31 | 15 | 3.34 |
| 41 | 15 | 5.78 |
| 51 | 15 | 10.3 |

TABLE 7-continued

Solubility of Racemic Calanolide A in Aqueous 2-Propanol.

| Temperature | [Water] | [Calanolide A] |
|---|---|---|
| 23 | 20 | 1.78 |
| 23 | 25 | 1.21 |
| 31 | 25 | 1.80 |
| 41 | 25 | 3.04 |
| 51 | 25 | 5.69 |
| 23 | 30 | 1.02 |
| 23 | 40 | 0.55 |
| 41 | 40 | 0.89 |
| 51 | 40 | 1.66 |
| 23 | 50 | 0.28 |

Both decreasing temperature and increasing water concentration were used to slowly reach the point of supersaturation in attempts to attain a slow, selective crystal growth. However, the selectivity obtained was not sufficient to form a basis for separation of calanolide B from calanolide A by this method alone. The calanolide B concentrations were enriched in the mother liquor, but only a minimal decreases in the levels in the isolated solids were observed. The results are shown in Table 8.

TABLE 8

Crystallization from Aqueous 2-Propanol.

| Evaluation | Crystallization Conditions | Starting Mat. | Isolated | M.L. | % Yield |
|---|---|---|---|---|---|
| | | % Cal A/ % Cal B | | | |
| KK | Add Water to 30 wt % over 100 min at 35° C. Filter at 23° C. | 86.8/11.6 | 88.4/11.6 | 59.2/34.3 | 81 |
| LL | Cool 15% Aqueous from 43° C. to 23° C. at 0.1° C./min. | 87.5/11.8 | 91.2/8.8 | 82.0/17.1 | 55 |
| MM | Add Water to 38 wt % over 4.8 h at 50° C. Filter at 50° C. | 87.5/11.8 | 90.8/9.2 | 76.6/20.5 | 67 |
| PP | Add Water to 15 wt % over 4.5 h at 23° C. Stir 3 days | 87.5/11.8 | 91.3/8.7 | 78.7/20.2 | 71 |

The overall separation process for removing racemic calanolide A from calanolide B is outlined in FIG. 5.

FIG. 5. Removal of Calanolide B from Calanolide A by Crystallization from Toluene.

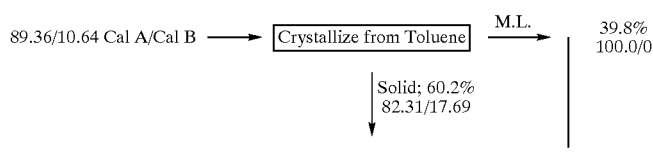

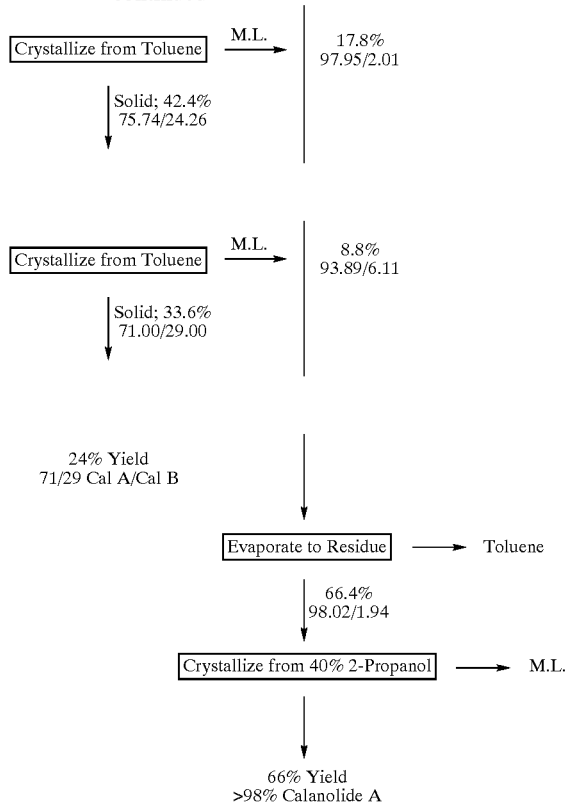

The solid was recrystallized from toluene three times to end up with material that contained 29% of calanolide B. Included in FIG. 5 is the percent of the total amount of starting material for each fraction, calculated from the calanolide A/calanolide B ratios of each of the streams. The amount collected in the mother liquor dropped by a factor of two for each recrystallization, and the calanolide B level in the mother liquor increased with each recrystallization. The overall recovery of the isolated solid from toluene was 24%.

The combined mother liquors, containing 1.94% of calanolide B, were crystallized from 40% aqueous 2-propanol to give a 65.6% recovery of racemic calanolide A containing 1.77% of calanolide B. Vacuum drying at up to 40° C. gave a solid containing 4.26 wt % water by Karl Fisher analysis.

Based on the crystallization characteristics of the mixture of diastereomers, toluene was found to be effective in removing calanolide B as a crystalline solid in a mixture up to approximately a 1/1 ratio of calanolide A to calanolide B. This depleted the calanolide B level in the mother liquor to, in some cases, less than 1%. By repeated recrystallization from toluene and collection of the mother liquors, a 66% recovery of 98.2% pure racemic calanolide A was obtained from feed containing 10.6% of calanolide B. Aqueous-2-propanol, which was found to deplete the level of calanolide B in the isolated solid but not at a level to be useful as a sole separation method, was used to isolate the purified racemic calanolide A from the combined mother liquors.

A two-step scaleable process has been developed to produce racemic calanolide A in a similar yield to the original procedure without the need for two chromatographic purifications. The intermediate aldol product does not need to be isolated and thus does not require purification. This process also does not require a Mitsunobu reaction and thus eliminates the need for chromatography to remove Mitsunobu by-products. Crystallization of the racemic calanolide A obtained from a borohydride reduction of the ketone increased the level of calanolide B in the isolated solid, and so decreased the calanolide B level in the mother liquor

EXAMPLES

Raw materials and solvents were obtained from Aldrich Chemical, Alfa, or Fisher Scientific. Melting points were measured using a Thomas Hoover capillary melting point apparatus, and are uncorrected. HPLC analysis was carried out at $\lambda=312$ nm by injecting a 2 to 10 $\mu$L sample dissolved in mobile phase onto a 25 cm×4.6 mm Diazem Phenyl II column eluting at 1 mL/min with 68% acetonitrile, 32% water adjusted to a pH of 2.5 to 3.5 with phosphoric acid (System A). Alternatively, a 25 cm×4.6 mm Zorbax SB-Phenyl column with a 1.5 mL/min flow of 70% acetonitrile, 30% water adjusted to a pH of 2.5 to 3.5 with phosphoric acid was used (System B). Approximate retention times for both systems are listed in Table 9.

TABLE 9

Reversed Phase HPLC Retention Times.

| Compound | R.T. min System A | R.T. min System B |
| --- | --- | --- |
| 4 | 10.9 | 4.9 |
| 5 | 6.3 | 2.7 |
| 6 | 8.2 | 3.2 |
| 9 | 6.3 | 2.5 |
| 10 | 7.6 | 3.0 |
| Calanolide A | 7.5 | 7.2 |
| Calanolide B | — | 6.7 |

Chiral HPLC analysis was carried out at $\lambda=312$ nm by injecting a 10 $\mu$L sample dissolved in mobile phase onto a 25 cm×4.6 mm Daicel Chiralpak AD column and eluting at 1 mL/min with 2.5 vol % methanol in pentane. Under these conditions, the calanolide A isomers eluted at 17.7 and 20.6 minutes, and the calanolide B isomers eluted at 17.7 and 24.7 minutes (approximate retention times).

Example 1

Preparation of Ketone 6

A 1-L jacketed bottom-drain reactor under nitrogen was charged with 44.4 g (0.130 mol) of chromene 4 (hereinafter referred to as Starting Material D or "SMD") and 835 mL of methylene chloride. The jacket was chilled to −15 to −20° C. At an internal temperature of −18° C., 51 mL (0.47 mol) of titanium tetrachloride was added dropwise over 50 minutes; the maximum temperature reached during the addition was −15° C. Diisopropylethylamine (60 mL, 0.34 mol) was added dropwise over one hour, the maximum temperature reached was −5° C. The black solution was stirred at approximately −17° C. for 30 minutes before the addition of 45 mL (0.80 mol) of acetaldehyde in three 15 mL portions over approximately 10 minutes. The maximum temperature reached during the addition was −5° C. The dark solution was stirred for one hour at −17° C. The solution was added to 600 mL of water containing 180 g of ammonium chloride. The lower organic phase was washed with 140 mL of water containing 11 mL of 37% hydrochloric acid HPLC analysis found 95.8 area % of 5 and 1.4 area % of 4. The dark solution was dried with 44 g of magnesium sulfate and the solution was filtered. The solvent was removed using a rotary evaporator with a bath temperature of 25° C. THF (70 g) was added, and the solvent was removed to a residual oil of 91.3 g. The oil was dissolved in 620 g of THF in a 1-L round-bottom flask, and the solution was chilled in an ice bath for the addition of 45 g (0.38 mol) of dimethylformamide dimethylacetal. After stirring at ambient temperature overnight, HPLC analysis found 3.0 area % of 9,39.6 area % of 10, and 47.6 area % of 6. The mixture was cooled in an ice bath, and 60 mL of saturated brine and 90 mL of water were added. The lower aqueous phase was drained, and the solvent was removed from the organic phase using a rotary evaporator with a bath temperature of 25° C. to a residue of 107.8 g. The residue was treated with 54 g of triethylamine, and the solvent was removed to a residue of 99 g. The dark red semi-solid residue was dissolved in 130 g of triethylamine containing 12 g of t-amyl alcohol, and the mixture was transferred to a 1-L bottom-drain jacketed reactor. HPLC analysis found 25.2 area % of 10 and 59.3 area % of 6. After the slurry was warmed to 40° C. and stirred for 8 hours HPLC analysis found 11.5 area % of 10 and 77.0 area % of 6. HPLC analysis of the supernate found 26.9 area % of 10 and 55.8 area % of 6. The slurry was cooled to 20° C. and stirred for 3 hours before the solid was isolated by vacuum filtration and washed 10 g of t-amyl alcohol. HPLC analysis of the isolated solid found 93.2 area % of 6 and 5.6 area % of 10; the mother liquor contained 19.4 area % of 10 and 31.5 area % of 6. The wetcake (24.7 g) was charged to a 250-mL round-bottom flask with 75.8 g of ethanol 2B, and the slurry was warmed to reflux, then cooled in an ice bath. The solid was isolated by vacuum filtration and rinsed with 10 g of ethanol 2B to give 22.51 g of 6 (95.9 area % 6, 3.4 area % of 10). The ethanol mother liquor contained 55.1 area % of 10 and 33.1 area % of 6. The solid was treated a second time with 78 g of ethanol 2B at reflux to afford 21.45 g of 6 (0.0582 mol, 45% yield, 97.2 area of 6, 2.2 area % of 10. The ethanol mother liquor contained 43.3area % of 10 and 48.6 area % of 6.

Example 2

Preparation of Racemic Calanolide A

A 1-L bottom-drain reactor with an overhead stirrer and nitrogen bubbler was charged with 21.4 g of 6 prepared above (0.0578 mol, 97.2 area % of 6, 2.2 area % of 10), 34.4 g (0.092 mol) of cerium chloride heptahydrate, and 206 g of ethanol 2B. The slurry was cooled to an internal temperature of −18° C., and 3.38 g (0.0893 mol) of powdered sodium borohydride was added in three approximately equal portions over approximately 30 minutes. The maximum temperature reached during the additions was −16° C. HPLC analysis 30 minutes after the additions found 72.7 area % of calanolide and 26.4 area % of 6. After four hours at −18° C., the levels were 96.5 and 2.3 area %, respectively. The slurry was stirred at the same temperature overnight, then quenched by the addition of 10 mL of acetone. The reaction mixture was added to 350 mL of water containing 35 g of ammonium chloride, and the product extracted into 350 mL of toluene. Chiral HPLC analysis found 48.6 area % of calanolide A and calanolide B (one peak), 44.0 area % of calanolide A, and 5.6 area % of calanolide B. The toluene solution was dried with 20 g of magnesium sulfate, the mixture was filtered, and the solvent was removed by rotary evaporation to give a yellow oil of 22.89 g. Addition of 60 mL of methyl t-butyl ether (MTBE) gave a slurry at ambient temperature. The slurry was chilled in an ice bath and the product was isolated by vacuum filtration and rinsed with 10 mL of MTBE to afford 8.27 g (0.0222 mol, 38% yield) of (+/−)-calanolide A (Reversed Phase HPLC: 99.0 area %; Chiral HPLC: 48.9 area % of calanolide A and calanolide B (one peak), 41.7 area % of calanolide A, and 9.35 area % of calanolide B). The mother liquor was concentrated to approximately ½ volume to afford a second crop of 7.54 g (0.0202 mol, 35% yield) of (+/−)calanolide A (Reversed Phase HPLC: 99.8 area %; Chiral HPLC: 49.1 area % of calanolide A and calanolide B (one peak), 49.1 area % of calanolide A, and 1.1 area % of calanolide B). The final mother liquor residue weighed 3.0 g (Reversed Phase HPLC: 88.4 area % of calanolide A; Chiral HPLC: 33.7 area % of calanolide A and calanolide B (one peak), 28.0 area % of calanolide A, and 4.2 area % of calanolide B).

Example 3

Removal of Calanolide B from Calanolide A by Crystallization

A 1-L bottom-drain jacketed reactor with overhead stirring was charged with 49.4 g of racemic calanolide A (89.36 area % calanolide A. 10.64 area % calanolide B) and 150 g of toluene. The mixture was heated to 56° C. to give a solution, then cooled at a rate of 0.1° C./min to −8° C. and held for 5 hours. HPLC analysis of the supernate found 100 area % of calanolide A. The solid was isolated by vacuum filtration arid washed with 14 g of toluene to give a 26;96 g wetcake (82.31 area % calanolide A, 17.69 area % calanolide B). The mother liquor (99.90 area % calanolide A) was evaporated to a residue of 20.8 g. The 26.96 g toluene wetcake was charged with 76 g of toluene into the 1-L reactor and heated to 50° C. to give a solution. The solution was cooled to 25° C. at a rate of 1° C./min. Crystallization began at approximately 33° C. The slurry was cooled to −8° C. at 0.50° C./min and held for approximately 1 hour. HPLC analysis of the supernate found 98.27 area % calanolide A and 1.69 area % calanolide B. The solid was isolated by vacuum filtration and washed with 7 g of toluene to give a 22.81 g wetcake (75.74 area % calanolide A, 24.26 area % calanolide B). The mother liquor (97.95 area % calanolide A, 2.01 area % calanolide B) was combined with the previous mother liquor and evaporated to a residue of 32.1 g. The 22.81 g wetcake was charged with 75 g of toluene into the 1-L reactor and heated to 50° C. to give a solution, then cooled to 25° C. to give a slurry. The slurry was cooled at a rate of 0.1° C./min to −9° C. and held for 9 hours. HPLC analysis of the supernate found 95.84 area % of calanolide A and 4.17 area % of calanolide B. The solid was isolated by vacuum filtration, washed with 7 g of toluene, and dried at 40° C. under vacuum to give 11.96 g (24 wt % recovery, 71.00 area % calanolide A, 29.00 area % calanolide B). The mother liquor (93.89 area % calanolide A, 6.11 area % calanolide B) was combined with the previous mother liquors and evaporated to a residue of 39.0 g (98.02 area % calanolide A, 1.94 area % calanolide B). To the solid in a 500-mL round-bottom flask with overhead stirring was added 200 g of 2-propanol, and the mixture was warmed to 50° C. to give a light slurry. Water (130 mL) was added dropwise over 30 minutes to give a white slurry. The slurry was chilled in an ice bath and the solid was collected by vacuum filtration, washed with 20 g of 60% aqueous 2-propanol, and dried under vacuum first at ambient temperature, then at 40° C. to give 33.89 g of racemic calanolide A (4.26 wt % water by Karl Fisher, 65.6% recovery corrected for water content, 98.23 area % calanolide A, 1.77 area % calanolide B, mp 113–7° C.). The mother liquor and wash solution (91.00 area % calanolide A, 6.58 area % calanolide B) was evaporated to give a residue of 1.5 g.

What is claimed is:

1. A process for synthesizing a trans-calanolide A ketone intermediate comprising the steps of:
   1) reacting a chromene intermediate in methylene chloride solution, stepwise, with titanium tetrachloride followed by diisopropylethylamine, followed by acetaldehyde;
   2) treating the aldol intermediate produced with a dehydration reagent to form a mixture of cis and trans cyclic ketones;
   3) equilibrating the cis and trans cyclic ketones with a base in a solvent to create a precipitate of the trans form; and
   4) isolating the crystalline ketone via filtration.

2. A method for removing a racemic calanolide B diastereomer from a mixture of racemic calanolide A and calanolide B diastereomers comprising the steps of:
   1) repeatedly crystallizing the mixture from solvents in which the calanolide B has a lower solubility than calanolide A;
   2) collecting a concentrating the combined mother liquors which are enriched in calanolide A and depleted in calanolide B; and
   3) recrystallizing the combined mother liquor residue from a solvent to remove the residual calanolide B and isolate purified racemic calanolide A.

3. The process of claim 1, wherein the dehydration reagent comprises dimethylformamide dimethylacetal in tetrahydrofuran.

4. The process of claim 1, wherein the base of step 3) comprises triethylamine.

5. The process of claim 4, wherein the base is dissolved in a solvent comprising t-amyl alcohol.

6. The method of claim 2, wherein the solvent of step 1) comprises toluene.

7. The method of claim 6, wherein the solvent of step 3) comprises aqueous 2-propanol.

* * * * *